US010920200B2

(12) United States Patent
Yao et al.

(10) Patent No.: US 10,920,200 B2
(45) Date of Patent: Feb. 16, 2021

(54) GLUCOSE OXIDASE CNGODA AND GENE AND APPLICATION THEREOF

(71) Applicant: FEED RESEARCH INSTITUTE, CHINESE ACADEMY OF AGRICULTURAL SCIENCES, Beijing (CN)

(72) Inventors: Bin Yao, Beijing (CN); Huiying Luo, Beijing (CN); Weina Liu, Beijing (CN); Jianzhong Ge, Beijing (CN); Tao Tu, Beijing (CN); Huoqing Huang, Beijing (CN); Xiaoyun Su, Beijing (CN); Yingguo Bai, Beijing (CN); Yuan Wang, Beijing (CN); Yaru Wang, Beijing (CN); Kun Meng, Beijing (CN)

(73) Assignee: FEED RESEARCH INSTITUTE, CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 16/608,833

(22) PCT Filed: Jun. 7, 2018

(86) PCT No.: PCT/CN2018/090245
§ 371 (c)(1),
(2) Date: Oct. 27, 2019

(87) PCT Pub. No.: WO2018/196881
PCT Pub. Date: Nov. 1, 2018

(65) Prior Publication Data
US 2020/0190484 A1    Jun. 18, 2020

(51) Int. Cl.
*C12N 9/04* (2006.01)
*C12N 15/81* (2006.01)

(52) U.S. Cl.
CPC ......... *C12N 9/0006* (2013.01); *C12N 15/815* (2013.01); *C12Y 101/03004* (2013.01)

(58) Field of Classification Search
None
See application file for complete search history.

(56) References Cited

U.S. PATENT DOCUMENTS 5,834,280 A * 11/1998 Oxenboll ............... A21D 8/042
435/190

OTHER PUBLICATIONS

Zhang et al., Structure 26:1474-1485, 2018 (Year: 2018).*
Sang, H., Mech. Dev., 121:1179-1186, 2004 (Year: 2004).*
Goswami et al., Front. Onc. 9:297, 2019, 25 pages (Year: 2019).*
"Pichia Expression Kit", Invitrogen Publication No. MAN0000012, 2014, 100 pages (Year: 2014).*
Ge et al., "Characterization, stability improvement, and bread baking applications of a novel cold-adapted glucose oxidase from Cladosporium neopsychrotolerans SL16", Food Chem. 310:125970, 2020, 8 pages (Year: 2020).*

* cited by examiner

*Primary Examiner* — David Steadman
(74) *Attorney, Agent, or Firm* — Patshegen IP LLC; Moshe Pinchas

(57) ABSTRACT

Provided are a glucose oxidase CnGODA, an encoding gene thereof, a recombinant expression vector comprising the gene, and a recombinant strain; the amino acid sequence of the glucose oxidase CnGODA is as represented in SEQ ID NO:1 or SEQ ID NO:2. Further provided is a method for use in preparing glucose oxidase CnGODA, and application of glucose oxidase CnGODA.

3 Claims, 2 Drawing Sheets
Specification includes a Sequence Listing.

GLUCOSE OXIDASE CNGODA AND GENE AND APPLICATION THEREOF

The Sequence Listing is submitted as an ASCII text file, created on Aug. 7, 2020, 15.0 KB, which is incorporated by reference herein.

FIELD OF THE INVENTION

The present invention relates to the field of genetic engineering, particularly to a glucose oxidase CnGODA, encoding gene and application thereof.

BACKGROUND OF THE INVENTION

Glucose oxidase is a flavin-dependent aerobic dehydrogenase that specifically oxidizes β-D-glucose in an aerobic environment to produce glucosinic acid and hydrogen peroxide. Glucose oxidase is widely distributed in animals, plants and microorganisms. Microorganisms become the main source of glucose oxidase because of its properties of rapid growth and reproduction, wide source.

Glucose oxidase has great potential application value as one of feed additives. In addition, glucose oxidase has broad application prospects, because of its specific catalytic property and high efficiency, and has been widely applied in food, feed, medicine, test paper and biosensor and other fields.

Order of the Invention

One order of the present invention is to provide a novel glucose oxidase.

Another order of the present invention is to provide a gene encoding the above glucose oxidase.

Another order of the present invention is to provide a recombinant vector comprising the gene encoding the above glucose oxidase.

Another order of the present invention is to provide a recombinant cell comprising the gene encoding the above glucose oxidase.

Another order of the present invention is to provide a method of preparing the above glucose oxidase.

Another order of the present invention is to provide applications of the above glucose oxidase.

SUMMARY OF THE INVENTION

Thus, in one aspect, the present invention is to overcome the defectives of the prior art to provide a novel glucose oxidase which is selected from:

(a) a polypeptide comprising the amino acids as shown in SEQ ID NO:1 or SEQ ID NO:2; or (b) a polypeptide with glucose oxidase activity having 75% to 99% homology with that shown by SEQ ID NO:1 or SEQ ID NO:2, and said polypeptide is derived from SEQ ID NO:1 or SEQ ID NO:2 by substitution, deletion and/or insertion of one or more amino acid residues.

```
SEQ ID NO. 1:
  1   MHSIHFLAAF LAAVSEALPN QTRADKAHAI TTNVDQVSNK TFDYIVCGGG

51   LTGLVVASRL SEDPNISVLV IENGEDDHED PRVNDVRTYG EAFKSDLDYN

101   LTSTPVPWQN DTGLLLVAGR TLGGSGSLNG ASWTKGDRTQ YDLLPVLSGD

151   DSWSFDALNE IMLGIEEFHE PTEEQIAKGA QYADEYHGRD GVVQVSFPAG

201   MFGGIQLSAL EASTLVWKGL KLVADFAAGV TSGATIIPNM VEPNDSQNRS

251   SPFTVYAKHQ TQERSNFLIL TGHRVTSINW RNGTGMVADG VTFQACRECE

301   VHTATTKREV LLAAGSLQSP QLLELSGVGD PEVLAAAYVP LKLCSPNVGK

351   NMQEQTKNTL WFDPISTDFD GSGPPNAVAF PDVHQLFKND SASIYKSIIS

401   SLEGYSQNLT AAGIVTNATA TRLILEAQVN NLWKDNAGAA EIFFVTSPTT

451   GQVGIDLWNL IVLSRGYVHI TSNSSWDHPQ IEPSYFGHPF DLEIQLAATK

501   QSREVSQTEP LASLISAETF PGFDEVPQNA TDDVWEQWVK ETFTSVWHYI

551   ATLGMMKEEL GGVVDSRLKV YGIENVRAVD ASVLPIQLSA HLSSSLYGIA

601   EKAAMMIKED QGH
```

According to an embodiment of the present invention, said glucose oxidase has a theoretical molecular weight of 64.733 kDa, and comprises 614 amino acids with a signal peptide of 17 amino acids, "MHSIHFLAAF LAAVSEA", in N-terminal, as set in forth in SEQ ID NO:3. Thereof, the mature glucose oxidase protein has the amino acids as shown in SEQ ID NO:2.

```
  1  LPNQTRADKA HAITTNVDQV SNKTFDYIVC GGGLTGLVVA SRLSEDPNIS

51  VLVIENGEDD HEDPRVNDVR TYGEAFKSDL DYNLTSTPVP WQNDTGLLLV

101  AGRTLGGSGS LNGASWTKGD RTQYDLLPVL SGDDSWSFDA LNEIMLGIEE

151  FHEPTEEQIA KGAQYADEYH GRDGVVQVSF PAGMFGGIQL SALEASTLVW

201  KGLKLVADFA AGVTSGATII PNMVEPNDSQ NRSSPFTVYA KHQTQERSNF

251  LILTGHRVTS INWRNGTGMV ADGVTFQACR ECEVHTATTK REVLLAAGSL

301  QSPQLLELSG VGDPEVLAAA YVPLKLCSPN VGKNMQEQTK NTLWFDPIST

351  DFDGSGPPNA VAFPDVHQLF KNDSASIYKS IISSLEGYSQ NLTAAGIVTN

401  ATATRLILEA QVNNLWKDNA GAAEIFFVTS PTTGQVGIDL WNLIVLSRGY

451  VHITSNSSWD HPQIEPSYFG HPFDLEIQLA ATKQSREVSQ TEPLASLISA

501  ETFPGFDEVP QNATDDVWEQ WVKETFTSVW HYIATLGMMK EELGGVVDSR

551  LKVYGIENVR AVDASVLPIQ LSAHLSSSLY GIAEKAAMMI KEDQGH
```

The glucose oxidase according to the embodiment was very stable between pH 6.0 and pH 10.0, can maintain more than 70% of the activity, and has the optimal pH of 7.0; and was thermostable, has the optimal temperature of 30° C., and can maintain more than 50% of the activity between 15° C. to 50° C.

In another aspect, the polypeptide of the glucose oxidase provided by the present invention are derived from the polypeptide comprising the amino acids as shown in SEQ ID NO:1 or SEQ ID NO:2 by substitution, deletion and/or insertion of one or more (e.g., one or several, a value selected from 1-10, e.g., 1, 2, 3, 4, 5, 6, 7, 8, 9 or 10, or ranges intermediated to the above-recited values) amino acid residues, and maintains the glucose oxidase activity. For example, a common strategy is conservative amino acid substitutions that the amino acid residue is replaced with an amino acid residue having a similar side chain without effect on the activity of the glucose oxidase. Families of amino acid residues having similar side chains have been defined in the art. Furthermore, it is well known in the art that during the cloning of genes, usually enzyme recognition sites are designed, which would result in one or several non-relating amino acid residues on the ends of target protein without affecting the activity thereof. According to the embodiment of the present invention, in order to construct a fusion protein, to enhance expression of recombinant protein, to obtain an recombinant protein automatically secreted outside the host cell, or to aid in the purification of the recombinant protein, suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions in the proteins.

In a preferred embodiment, a glucose oxidase is such an active protein that is at least about 75%, 76%, 77%, 78%, 79%, or at least about, or at least about 80%, 81%, 82%, 83%, 84%, 85%, 86%, 87%, 88%, 89%, or at least about 90%, 91%, 92%, 93%, 94%, 95%, 96%, 97%, 98%, more preferably at least about 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to the full amino acid sequence as shown in SEQ ID NO:1 or SEQ ID NO:2. Ranges and identity values intermediated to the above-recited values (e.g., 75-90% homologous or 98.1-99.9% identical) are also intended to be included in the present invention.

Yet another aspect of the invention is to provide a gene encoding the above glucose oxidase, with the following characteristics of:
(a) encoding a polypeptide comprising the amino acids as shown in SEQ ID NO: 1 or SEQ ID NO: 2;
(b) encoding a polypeptide with glucose oxidase activity which is derived from SEQ ID NO: 1 or SEQ ID NO: 2 by substitution, deletion and/or insertion of one or more amino acid residues.

Preferably, the gene encoding the above glucose oxidase according to one embodiment of the present invention is selected from
(a) DNA comprising a nucleotide sequence set in forth in SEQ ID NO:3 or SEQ ID NO:4; or
(b) DNA having 75% to 99% homology with that shown in SEQ ID NO:3 or SEQ ID NO:4, hybridizing under stringent conditions to a nucleotide as set in forth in SEQ ID NO:3 or SEQ ID NO:4, and encoding polypeptide with same glucose oxidase activity as that of SEQ ID NO:1 or SEQ ID NO:2.

```
SEQ ID NO. 3:
  1  ATGCATTCGA TTCATTTCCT AGCTGCTTTC CTGGCTGCAG TCTCTGAAGC TCTTCCCAAT

61  CAAACGCGAG CTGACAAAGC CCATGCCATC ACTACAAACG TCGACCAGGT CTCAAACAAA

121  ACTTTCGACT ACATAGTCTG CGGCGGAGGC TTGACAGGCC TGGTCGTCGC AAGTCGGTTG

181  TCAGAAGACC CAAATATATC TGTTCTCGTC ATTGAGAACG GAGAGGACGA CCACGAAGAC

241  CCTCGCGTGA ACGACGTGAG AACCTACGGA GAAGCCTTCA AATCCGACCT CGACTACAAC
```

```
 301   CTCACATCAA CCCCAGTACC ATGGCAGAAC GACACAGGTC TACTTCTTGT GGCTGGCAGG
 361   ACACTTGGTG GAAGTGGCAG TCTCAATGGT GCCAGCTGGACTAAAGGCGA CAGGACGCAG
 421   TATGATTTGC TCCCGGTCTT GAGCGGCGAT GACTCGTGGT CCTTCGATGC TTTGAACGAG
 481   ATCATGCTAG GCATTGAAGAGTTCCACGAA CCGACTGAAG AACAGATTGC CAAAGGTGCA
 541   CAGTATGCAG ACGAATACCA TGGCCGTGAC GGAGTTGTCC AAGTCTCCTT CCCAGCTGGC
 601   ATGTTCGGCG GCATTCAACT TTCGGCTTTG GAAGCTTCCA CTCTCGTCTG GAAGGGCCTG
 661   AAACTTGTCG CGGACTTTGC AGCCGGAGTG ACAAGTGGTGCGACCATCAT CCCAAACATG
 721   GTTGAGCCAA ACGACTCCCA AAATCGGTCT TCCCCATTCA CGGTCTATGC CAAGCACCAG
 781   ACTCAGGAAC GCAGCAACTTCTTGATCTTG ACAGGACACC GTGTGACATC CATCAACTGG
 841   CGCAACGGCA CTGGCATGGT AGCTGATGGT GTCACATTTC AAGCATGCCG CGAATGCGAG
 901   GTACACACAG CCACGACAAA GCGAGAAGTA CTGCTCGCCG CGGGCTCGTT GCAGAGCCCA
 961   CAGCTTCTCG AGCTCTCTGG CGTGGGTGAT CCTGAGGTCTTGGCCGCCGC ATATGTTCCT
1021   CTGAAGCTGT GTTCTCCCAA TGTTGGTAAG AACATGCAGG AACAGACCAA AAACACTCTC
1081   TGGTTCGACC CCATCAGCACCGATTTCGAT GGTTCCGGAC CTCCAAACGC AGTTGCTTTC
1141   CCGGACGTCC ACCAACTGTT CAAAAATGAC AGTGCAAGCA TTTACAAATC TATCATTTCC
1201   AGCCTCGAAG GATACTCACA AAACCTGACC GCCGCCGGCA TCGTCACAAA CGCCACAGCA
1261   ACACGCCTCA TCCTTGAAGC ACAAGTCAAC AACCTCTGGAAAGATAACGC CGGAGCAGCA
1321   GAGATCTTCT TCGTGACTTC ACCCACCACA GGCCAAGTTG GCATTGATCT CTGGAACCTC
1381   ATCGTCCTGT CCCGAGGCTACGTGCACATC ACTTCGAACT CCTCCTGGGA CCACCCCCAA
1441   ATCGAGCCCT CCTACTTCGG CCACCCTTTC GACCTTGAGA TTCAGCTCGC AGCCACCAAG
1501   CAATCACGCG AAGTCTCCCA AACAGAACCT CTCGCCTCGC TCATCAGCGC CGAGACATTT
1561   CCTGGTTTCG ATGAAGTGCC GCAAAATGCC ACAGACGATGTGTGGGAGCA GTGGGTTAAG
1621   GAGACGTTCA CATCTGTTTG GCACTACATA GCTACATTGG GCATGATGAA AGAGGAATTG
1681   GGTGGTGTTG TGGACAGCAGGCTGAAGGTA TATGGCATTG AGAATGTACG AGCGGTGGAT
1741   GCTAGTGTGC TGCCGATCCA GCTTTCGGCG CACTTGAGCT CTTCGCTGTA CGGCATTGCG
1801   GAGAAGGCTG CTATGATGAT TAAGGAAGAT CAGGGACATT GA
```

Preferably, the cDNA of the said gene has full length of 1842 bp comprising an oligonucleotide sequence encoding the signal peptide, "ATGCATTCGA TTCATTTCCT AGCTGCTTTC CTGGCTGCAG TCTCTGAAGC T", and the gene encoding the mature glucose oxidase protein is as set in forth in SEQ ID NO:4.

```
                                                              SEQ ID NO. 4
   1   CTTCCCAATC AAACGCGAGC TGACAAAGCC CATGCCATCA CTACAAACGT CGACCAGGTC
  61   TCAAACAAAA CTTTCGACTA CATAGTCTGC GGCGGAGGCTTGACAGGCCT GGTCGTCGCA
 121   AGTCGGTTGT CAGAAGACCC AAATATATCT GTTCTCGTCA TTGAGAACGG AGAGGACGAC
 181   CACGAAGACC CTCGCGTGAACGACGTGAGA ACCTACGGAG AAGCCTTCAA ATCCGACCTC
 241   GACTACAACC TCACATCAAC CCCAGTACCA TGGCAGAACG ACACAGGTCT ACTTCTTGTG
 301   GCTGGCAGGA CACTTGGTGG AAGTGGCAGT CTCAATGGTG CCAGCTGGAC TAAAGGCGAC
 361   AGGACGCAGT ATGATTTGCT CCCGGTCTTG AGCGGCGATGACTCGTGGTC CTTCGATGCT
 421   TTGAACGAGA TCATGCTAGG CATTGAAGAG TTCCACGAAC CGACTGAAGA ACAGATTGCC
 481   AAAGGTGCAC AGTATGCAGACGAATACCAT GGCCGTGACG GAGTTGTCCA AGTCTCCTTC
 541   CCAGCTGGCA TGTTCGGCGG CATTCAACTT TCGGCTTTGG AAGCTTCCAC TCTCGTCTGG
```

-continued

```
 601   AAGGGCCTGA AACTTGTCGC GGACTTTGCA GCCGGAGTGA CAAGTGGTGC GACCATCATC

661   CCAAACATGG TTGAGCCAAA CGACTCCCAA AATCGGTCTT CCCCATTCAC GGTCTATGCC

721   AAGCACCAGA CTCAGGAACG CAGCAACTTC TTGATCTTGA CAGGACACCG TGTGACATCC

781   ATCAACTGGC GCAACGGCACTGGCATGGTA GCTGATGGTG TCACATTTCA AGCATGCCGC

841   GAATGCGAGG TACACACAGC CACGACAAAG CGAGAAGTAC TGCTCGCCGC GGGCTCGTTG

901   CAGAGCCCAC AGCTTCTCGA GCTCTCTGGC GTGGGTGATC CTGAGGTCTT GGCCGCCGCA

961   TATGTTCCTC TGAAGCTGTG TTCTCCCAAT GTTGGTAAGAACATGCAGGA ACAGACCAAA

1021   AACACTCTCT GGTTCGACCC CATCAGCACC GATTTCGATG GTTCCGGACC TCCAAACGCA

1081   GTTGCTTTCC CGGACGTCCACCAACTGTTC AAAAATGACA GTGCAAGCAT TTACAAATCT

1141   ATCATTTCCA GCCTCGAAGG ATACTCACAA AACCTGACCG CCGCCGGCAT CGTCACAAAC

1201   GCCACAGCAA CACGCCTCAT CCTTGAAGCA CAAGTCAACA ACCTCTGGAA AGATAACGCC

1261   GGAGCAGCAG AGATCTTCTT CGTGACTTCA CCCACCACAGGCCAAGTTGG CATTGATCTC

1321   TGGAACCTCA TCGTCCTGTC CCGAGGCTAC GTGCACATCA CTTCGAACTC CTCCTGGGAC

1381   CACCCCCAAA TCGAGCCCTCCTACTTCGGC CACCCTTTCG ACCTTGAGAT TCAGCTCGCA

1441   GCCACCAAGC AATCACGCGA AGTCTCCCAA ACAGAACCTC TCGCCTCGCT CATCAGCGCC

1501   GAGACATTTC CTGGTTTCGA TGAAGTGCCG CAAAATGCCA CAGACGATGT GTGGGAGCAG

1561   TGGGTTAAGG AGACGTTCAC ATCTGTTTGG CACTACATAGCTACATTGGG CATGATGAAA

1621   GAGGAATTGG GTGGTGTTGT GGACAGCAGG CTGAAGGTAT ATGGCATTGA GAATGTACGA

1681   GCGGTGGATG CTAGTGTGCTGCCGATCCAG CTTTCGGCGC ACTTGAGCTC TTCGCTGTAC

1741   GGCATTGCGG AGAAGGCTGC TATGATGATT AAGGAAGATC AGGGACATTG A
```

According to an embodiment of the present invention, the mature protein with molecular weight of 64.733 kDa belongs to the glucose/methanol/choline REDOX enzyme family. And, the glucose oxidase and the gene encoding it are confirmed to be novel by BLAST.

In another embodiment, the protein with glucose oxidase activity according to the present invention comprises the amino acid sequence which is encoded by a nucleotide sequence which hybridizes under stringent conditions to the nucleotide sequence as set forth in SEQ ID NO: 3 or SEQ ID NO: 4. As used herein, the term "hybridizes under stringent conditions" is intended to describe conditions for hybridization and washing under which the nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to one of the ordinary skills in the art and can be found in *Current Protocols in Molecular Biology*, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50-65° C. A person skilled in the art understands that high stringent condition could be realized by raising the hybridization temperature up to 50° C., 55° C., 60° C. or 65° C.

Besides, it will be appreciated by one of the ordinary skills in the art that genetic polymorphism due to natural variation may exist among individuals within a population. Such natural variations can typically result in 1-5% variance in the nucleotide sequence of the gene encoding the glucose oxidase. Any and all such nucleotide variations and the amino acid polymorphisms in glucose oxidase resulted from natural variation that do not alter the functional activity of glucose oxidase proteins are intended to be within the scope of the present invention. Therefore, the present invention also encompasses a polypeptide with glucose oxidase activity encoded by such an allele or natural variant of the polynucleotide as shown in SEQ ID NO: 3 or SEQ ID NO:4

On the other hand, the present invention provides a novel glucose oxidase gene of SEQ ID NO:3 or SEQ ID NO:4. The present invention further encompasses nucleic acid molecules that differ from the nucleotide sequence depicted in SEQ ID NO:3 or SEQ ID NO:4 due to degeneracy of the genetic code and thus encode the same glucose oxidase protein. In another embodiment of the present invention, an isolated nucleic acid molecule is a nucleotide sequence which hybridizes under stringent conditions, to a nucleotide sequence as set in forth in SEQ ID NO:3 or SEQ ID NO:4, and preferably is the allele or natural variant thereof. In a preferred embodiment of the present invention, the nucleic acid molecule encodes a full glucose oxidase protein which is substantially homologous to an amino acid sequence of SEQ ID NO:1 or SEQ ID NO:2. For example, the said protein is derived from SEQ ID NO: 1 or SEQ ID NO:2 by substitution, deletion and/or insertion of one or more (e.g., one or several, or a value selected from 1-10) amino acid residues, or is at least 99% homologous to the amino acid sequence of SEQ ID NO:1 or SEQ ID NO:2. Such a nucleic acid molecule is preferably at least about 60%, 61%, 62%, 63%, 64%, 65%, 66%, 67%, 68%, 69%, or at least 70%, 71%, 72%, 73%, 74%, 75%, 76%, 77%, 78%, 79%, or at least about 80%, 81%, 82%, 83%, 84%, 85%, 86%, 87%, 88%, 89%, more preferably at least about 90%, 91%, 92%, 93%, 94%, 95%, 96%, 97%, 97.7%, 97.8%, 97.9%, or at least about 98%, 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to a nucleotide sequence of SEQ ID NO:3 or SEQ ID NO:4. Ranges and identity values intermediate to the above-recited values (e.g., 76-97% homologous or 97.8-99.9% identical) are also intended to be included in the present invention.

The recombinant expression vectors of the invention can be designed for expression of glucose oxidase proteins in prokaryotic or eukaryotic cells. For example, glucose oxidase gene can be expressed in yeast such as Pichia. In a preferred embodiment of the present invention, the glucose oxidase gene was inserted between the sites of EcoR I and Not of the vector pPIC9 to under the control and regulation of the promoter AOX1 to obtain the recombinant expression vector pPIC9-CngodA.

According to the embodiment of the present invention, the Vector DNA comprising the above glucose oxidase gene can be introduced into prokaryotic or eukaryotic cells via conventional transformation or transfection techniques in the art.

Thus, the present invention provides a host cell comprising the above glucose oxidase gene. According to the embodiment of the present invention, a prokaryotic or eukaryotic host cell in culture, can be used to produce (i.e., express) a glucose oxidase protein, wherein the said host preferably is *Pichiapastoris* cell, *Saccharomyces cerevisiae*, *Hansenulapolymorpha*, more preferabley *Pichiapastoris* cell to obtain the recombinant cell GS115/CngodA.

Accordingly, the invention further provides methods for producing glucose oxidase proteins using the host cells of the invention. In one embodiment, the method comprises culturing the host cell into which a recombinant expression vector encoding a glucose oxidase protein has been introduced, or into which genome has been introduced a gene encoding a wild-type or altered glucose oxidase protein in a suitable medium until glucose oxidase protein is produced. In another embodiment, the method further comprises isolating glucose oxidase proteins from the medium or the host cell.

In another aspect, the present invention provides the application of the above glucose oxidase to industry to produce the glucose oxidase by the industrial methods.

A novel glucose oxidase gene was first isolated from *Cladosporiumneopsychrotolerns* SL-16 strain according to the present invention, and it was the first time to find such enzyme in this species to expand the researching scope of glucose oxidase. The glucose oxidase of the present invention has good catalytic activity and is easy to be produced by ferment, which means that this novel glucose oxidase will have more important application value in feed, food, medicine and other industries.

BRIEF DESCRIPTIONS OF THE DRAWINGS

EMBODIMENT

Figure 1:
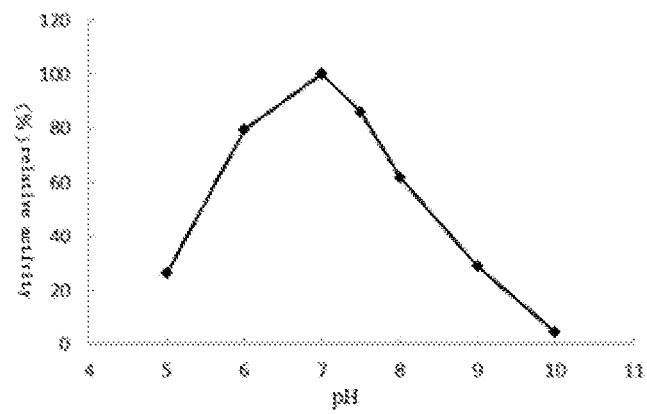
FIG. 1 shows optimum pH values for the recombinant glucose oxidase.

The present invention is further illustrated with reference to the following Examples and the appended drawings, which should by no means be construed as limitations of the present invention.

Test Materials and Reagents

1. Strains and vectors: *Pichia pastoris* strain GS115 (Invitrogen); and vetor pPIC9 (Invitrogen, San Diego, Calif.).

2. Enzymes and other biochemical reagents: restriction endonucleases (TaKaRa); ligase (Invitrogen); and birch xylan(Sigma) 3. Medium:

(1) Enzyme production medium (/L): 172.11 g of glucose, 11.05 g of corn syrup, 52.29 g calcium carbonate, 0.5 g of $(NH_4)H_2PO_4$, 0.125 g of $MgSO_4.7H_2O$, 0.125 g of $FeSO_4.7H_2O$, which are sterilized at 121° C. for 20 min.

(2) *E. coli*. LB medium: 1% of peptone, 0.5% of yeast extract, and 1% of NaCl, natural pH.

(3) BMGY medium: 1% of yeast extract; 2% of peptone; 1.34% of YNB, 0.00004% of Biotin; and 1% of glycerol(V/V).

(4) BMMY medium: 1% of yeast extract; 2% of peptone; 1.34% of YNB, 0.00004% of Biotin; and 0.5% of methanol (V/V).

Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Example 1 Cloning Glucose Oxidase Gene God from *Cladosporiumneopsychrotolerns* SL-16

(1) Isolating the Total RNA of *Cladosporiumneopsychrotolerns* SL-16

First, bacteria cells cultured in enzyme-producing medium for 3 days were collected on the filter paper and pressed dry, followed by adding liquid nitrogen to a high-temperature sterilized mortar and quickly ground the bacteria into powder. Then, the grounded powder was transferred to a centrifuge tube with 800 μL of Trizol, blended well and left in the room temperature for 5 min 200 L of chloroform was added, shaken violently for 15 s, placed at room temperature for 3 min, and centrifuged at 4° C. at 12,000 RPM for 15 min. The supernatant was obtained, and isopropanol of the equal volume was added to be mixed well, placed at room temperature for 10 min and centrifuged at 4° C. at 12,000 RPM for 10 min. The supernatant was removed and the precipitation was washed twice with 70% of ethanol followed by drying in the air for 5 min, and an appropriate amount of DNase/Rnase-free deionized water was added to dissolve RNA.

(2) Obtaining the cDNA Sequence Encoding the Glucose Oxidase

One chain of total cDNA was obtained with Oligo (dT) 20 and the reverse transcriptase, and then primers F and R (SEQ ID NO: 5 and 6, respectively) with EcoR I and Not I restriction sites were designed as list in the table 1 to perform PCR on the coding region of CnGODA mature protein to obtain the cDNA sequence of glucose oxidase.

TABLE 1

Primers

| Primer | SEQUENCE (5'---3') | Length (bp) |
|---|---|---|
| F | ACTGAATTCCTTCCCAATCA AACGCGAGCTGACAAAGCCC | 40 |
| R | GAGTGCGGCCGCTCAATGTC CCTGATCTTCCTTAATCATC | 40 |

Example 2 Preparing the Recombinant Cell Comprising Glucose Oxidase Gene (1) Constructing the expression vector and expressing in *Pichiapastoris* GS115 The expression vector pPIC9-CngodA comprising the full-length gene encoding glucose oxidase was constructed by inserting the gene at the downstream of the signal peptide of the plasmid to form the correct reading frame, followed to transform *Ecoli* cell Trans1 to screen the positive transformants for sequencing. The transformants with the correct sequence were used to prepare the recombinant plasmid in a large amount. The DNA of the expression vector was lined with restriction enzyme Bgl II, followed by electronically transforming *Pichia pastoris* strain GS115, and being cultured at 30° C. for 2 to 3 days to screen the transformants on the MD plate for expressing assays. The particular operation refers to *Pichia pastoris* expression manual.

The recombinant expression vector comprising the gene including the signal peptide was constructed as same as above.

(2) Screening the Transformants with High Glucose Oxidase Activity

The single colony on the MD plate was selected with a sterilized toothpick and numbered on the MD plates which were incubated at 30° C. for 1 to 2 days until the colony grown. The transformants were inoculated in a centrifuge tube containing 3 mL BMGY medium, and cultured according to their number, cultured at 30° C. and 220 RPM for 48 h followed by centrifuging at 3,000×g for 15 min to remove supernatant, and adding lint, BMMY medium containing 0.5% of methanol into the centrifuge tube for induction culturing at 30° C. and 220 RPM for 48 h to collect the supernatant by centrifuging at 3,000×g for 5 min for detecting the activity. Finally, the transformant with high glucose oxidase activity were screened out. The particular operation refers to *Pichia pastoris* expression manual.

Example 3 Recombinant *Pichia Pastoris* Fermenting to Produce Recombinant Enzyme The screened transformants were incubated in 300 mL of BMGY for 48 h at 30° C. and 220 rpm, and then the cells were spun down by centrifuging at 4,500 rpm for 5 min and suspended in 100 mL of BMMY containing 0.5% of methanol to induce the glucose oxidase gene expression for 72 hours with addition of methanol solution every 24 hours to keep concentration of methanol as 0.5% by compensating the loss of methanol. After induction, the supernatant was recovered by spinning at 12,000×g for 10 min to test the activity of the enzyme and performing SDS-PAGE.

(1) Purifying the Recombinant Glucose Oxidase

The supernatant of the recombinant glucose oxidase expressed in the shaking bottle was collected followed by being concentrated with 10 kDa membrane package while replacing the medium of the fermentation broth with low salt buffer, and further concentrated with 10 kDa ultrafiltration tube. The concentrated solution was further purified with ion exchange chromatography by loading 2.0 mL of CnGODA concentrate into HiTrap Q Sepharose XL anion column pre-balanced with 20 mMPBS (pH 6.9), and eluting with NaCL in linear gradient of 0 to 1 mol/L, to detect enzyme activity and determine protein concentration of the eluent collected step by step.

Example 4 Measuring the Properties of the Recombinant Glucose Oxidase

The activity of glucose oxidase was measured with a spectrophotometry by keeping 5 mL of the reaction system comprising 2.5 mL of adjacent anisidine buffer, 0.3 mL of 18% glucose solution, 0.1 mL of horseradish peroxidase is 90 U/mL, and 0.1 mL of appropriate diluted enzyme solution reacted at pH 6.0 and 30° C. for 3 min, followed by adding 2 mL of sulfuric acid in 2M to terminate the reaction, and determining the absorption value at $OD_{540}$ after cooling.

Definition of glucose oxidase activity unit (U): the enzyme amount decomposing 1 μmol of β-D-glucose into D-gluconic acid and hydrogen peroxide.

(1) Optimum pH Values and pH Stability for the Recombinant Glucose Oxidase

The glucose oxidase purified in example 2 was reacted in the different pHs to determine optimum pH. The adjacent anisidine solution with different pHs was prepared with the glycine-hydrochloric acid buffer with pH 1.0 to 3.0, and citric acid-disodium hydrogen phosphate buffer with pH 8.0 to 10.0, for determining the optimum pH at 30° C. As shown in FIG. 1, the activity of the recombinant glucose oxidase varied with pHs. The highest activity was observed at pH 7.0. The recombinant glucose oxidase was stable at pH 6.0 to 8.0 and maintained more than 90% of activity.

Figure 2:
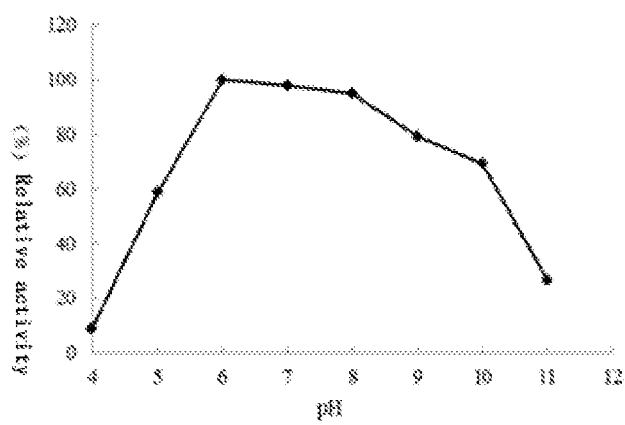
FIG. 2 shows pH stabilities for the recombinant glucose oxidase.

The pH stability of the glucose oxidase was researched by detecting its activity at optimum pH after being treated for 60 min at 25° C. and different pHs. As shown in FIG. 2, the recombinant glucose oxidase has good pH stability in that it maintains more than 80% of activity at pH 6.0 to 9.0, 60% and 70% of activity treated at pH 5.0 and 10.0 respectively.

(2) Optimum Temperature and Heat Stability for the Recombinant Glucose Oxidase

Figure 3:
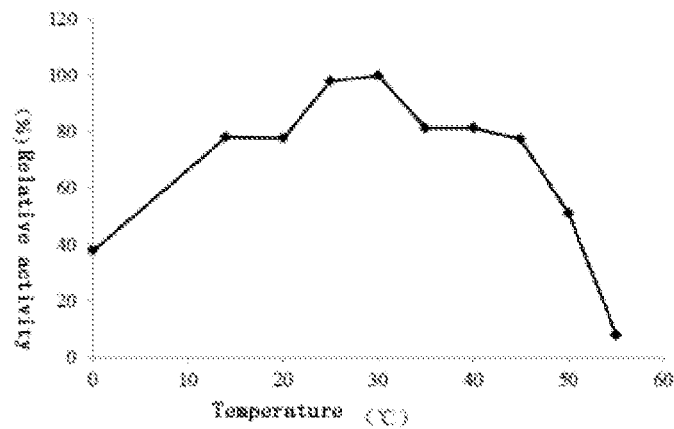
FIG. 3 shows optimum temperature for the recombinant glucose oxidase.

The glucose oxidase was reacted in the different temperatures from 0 to 55° C. at pH 6.0 to determine its optimum temperature. As shown in FIG. 3, the optimum temperature for this enzyme was 30° C., and it maintained more than 50% of activity between 15° C. and 50° C.

Figure 4:
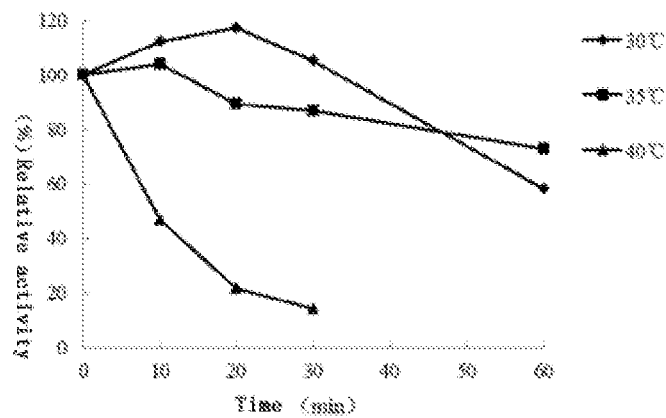
FIG. 4 shows thermostability for the recombinant glucose oxidase.

The thermostability was determined by detecting the enzyme activity of the glucose oxidase after being treated at 30° C., 35° C., 40° C. for the different time. As shown by FIG. 4, more than 70% of enzyme activity was kept after being treated at 35° C. for 60 min, but only 20% of enzyme activity was kept after being treated at 40° C. for 20 min.

The invention claimed is:

1. A method of producing glucose oxidase having the amino acid sequence of SEQ ID NO: 1 or SEQ ID NO: 2, comprising the steps of:

(1) transforming a prokaryotic or eukaryotic host cell in culture with a polynucleotide comprising a nucleotide sequence encoding said glucose oxidase to obtain a recombinant host cell;

(2) cultivating the recombinant host cell to induce expression of said glucose oxidase; and (3) isolating and recovering said glucose oxidase.

2. The method of claim 1, wherein the method further comprises the step of preparing a feed, food, medicine, test paper or biosensor comprising said glucose oxidase.

3. The method of claim 1, wherein said glucose oxidase has an optimal pH of 7.0, an optimal temperature of 30° C., pH stability within pH 6.0 to 9.0, and maintains more than 50% of activity between 15° C. and 50° C.

* * * * *

SEQUENCE LISTING

<160> NUMBER OF SEQ ID NOS: 6

<210> SEQ ID NO 1
<211> LENGTH: 613
<212> TYPE: PRT
<213> ORGANISM: Cladosporiumneopsychrotolerns SL-16 strain

<400> SEQUENCE: 1

```
Met His Ser Ile His Phe Leu Ala Ala Phe Leu Ala Ala Val Ser Glu
1               5                   10                  15

Ala Leu Pro Asn Gln Thr Arg Ala Asp Lys Ala His Ala Ile Thr Thr
            20                  25                  30

Asn Val Asp Gln Val Ser Asn Lys Thr Phe Asp Tyr Ile Val Cys Gly
        35                  40                  45

Gly Gly Leu Thr Gly Leu Val Val Ala Ser Arg Leu Ser Glu Asp Pro
    50                  55                  60

Asn Ile Ser Val Leu Val Ile Glu Asn Gly Glu Asp Asp His Glu Asp
65                  70                  75                  80

Pro Arg Val Asn Asp Val Arg Thr Tyr Gly Glu Ala Phe Lys Ser Asp
                85                  90                  95

Leu Asp Tyr Asn Leu Thr Ser Thr Pro Val Pro Trp Gln Asn Asp Thr
            100                 105                 110

Gly Leu Leu Leu Val Ala Gly Arg Thr Leu Gly Gly Ser Gly Ser Leu
        115                 120                 125

Asn Gly Ala Ser Trp Thr Lys Gly Asp Arg Thr Gln Tyr Asp Leu Leu
    130                 135                 140

Pro Val Leu Ser Gly Asp Asp Ser Trp Ser Phe Asp Ala Leu Asn Glu
145                 150                 155                 160

Ile Met Leu Gly Ile Glu Glu Phe His Glu Pro Thr Glu Glu Gln Ile
                165                 170                 175

Ala Lys Gly Ala Gln Tyr Ala Asp Glu Tyr His Gly Arg Asp Gly Val
            180                 185                 190

Val Gln Val Ser Phe Pro Ala Gly Met Phe Gly Gly Ile Gln Leu Ser
        195                 200                 205

Ala Leu Glu Ala Ser Thr Leu Val Trp Lys Gly Leu Lys Leu Val Ala
    210                 215                 220

Asp Phe Ala Ala Gly Val Thr Ser Gly Ala Thr Ile Ile Pro Asn Met
225                 230                 235                 240

Val Glu Pro Asn Asp Ser Gln Asn Arg Ser Ser Pro Phe Thr Val Tyr
                245                 250                 255

Ala Lys His Gln Thr Gln Glu Arg Ser Asn Phe Leu Ile Leu Thr Gly
            260                 265                 270

His Arg Val Thr Ser Ile Asn Trp Arg Asn Gly Thr Gly Met Val Ala
        275                 280                 285

Asp Gly Val Thr Phe Gln Ala Cys Arg Glu Cys Glu Val His Thr Ala
    290                 295                 300

Thr Thr Lys Arg Glu Val Leu Leu Ala Ala Gly Ser Leu Gln Ser Pro
305                 310                 315                 320

Gln Leu Leu Glu Leu Ser Gly Val Gly Asp Pro Glu Val Leu Ala Ala
                325                 330                 335

Ala Tyr Val Pro Leu Lys Leu Cys Ser Pro Asn Val Gly Lys Asn Met
            340                 345                 350

Gln Glu Gln Thr Lys Asn Thr Leu Trp Phe Asp Pro Ile Ser Thr Asp
        355                 360                 365
```

```
Phe Asp Gly Ser Gly Pro Pro Asn Ala Val Ala Phe Pro Asp Val His
    370             375                 380

Gln Leu Phe Lys Asn Asp Ser Ala Ser Ile Tyr Lys Ser Ile Ile Ser
385                 390                 395                 400

Ser Leu Glu Gly Tyr Ser Gln Asn Leu Thr Ala Ala Gly Ile Val Thr
                405                 410                 415

Asn Ala Thr Ala Thr Arg Leu Ile Leu Glu Ala Gln Val Asn Asn Leu
            420                 425                 430

Trp Lys Asp Asn Ala Gly Ala Ala Glu Ile Phe Phe Val Thr Ser Pro
                435                 440                 445

Thr Thr Gly Gln Val Gly Ile Asp Leu Trp Asn Leu Ile Val Leu Ser
    450                 455                 460

Arg Gly Tyr Val His Ile Thr Ser Asn Ser Ser Trp Asp His Pro Gln
465                 470                 475                 480

Ile Glu Pro Ser Tyr Phe Gly His Pro Phe Asp Leu Glu Ile Gln Leu
                485                 490                 495

Ala Ala Thr Lys Gln Ser Arg Glu Val Ser Gln Thr Glu Pro Leu Ala
            500                 505                 510

Ser Leu Ile Ser Ala Glu Thr Phe Pro Gly Phe Asp Glu Val Pro Gln
        515                 520                 525

Asn Ala Thr Asp Asp Val Trp Glu Gln Trp Val Lys Glu Thr Phe Thr
    530                 535                 540

Ser Val Trp His Tyr Ile Ala Thr Leu Gly Met Met Lys Glu Glu Leu
545                 550                 555                 560

Gly Gly Val Val Asp Ser Arg Leu Lys Val Tyr Gly Ile Glu Asn Val
                565                 570                 575

Arg Ala Val Asp Ala Ser Val Leu Pro Ile Gln Leu Ser Ala His Leu
            580                 585                 590

Ser Ser Ser Leu Tyr Gly Ile Ala Glu Lys Ala Ala Met Met Ile Lys
        595                 600                 605

Glu Asp Gln Gly His
        610

<210> SEQ ID NO 2
<211> LENGTH: 596
<212> TYPE: PRT
<213> ORGANISM: Cladosporiumneopsychrotolerns SL-16 strain

<400> SEQUENCE: 2

Leu Pro Asn Gln Thr Arg Ala Asp Lys Ala His Ala Ile Thr Thr Asn
1               5                   10                  15

Val Asp Gln Val Ser Asn Lys Thr Phe Asp Tyr Ile Val Cys Gly Gly
            20                  25                  30

Gly Leu Thr Gly Leu Val Val Ala Ser Arg Leu Ser Glu Asp Pro Asn
        35                  40                  45

Ile Ser Val Leu Val Ile Glu Asn Gly Glu Asp His Glu Asp Pro
    50                  55                  60

Arg Val Asn Asp Val Arg Thr Tyr Gly Glu Ala Phe Lys Ser Asp Leu
65                  70                  75                  80

Asp Tyr Asn Leu Thr Ser Thr Pro Val Pro Trp Gln Asn Asp Thr Gly
                85                  90                  95

Leu Leu Leu Val Ala Gly Arg Thr Leu Gly Ser Gly Ser Leu Asn
            100                 105                 110

Gly Ala Ser Trp Thr Lys Gly Asp Arg Thr Gln Tyr Asp Leu Leu Pro
        115                 120                 125
```

-continued

```
Val Leu Ser Gly Asp Asp Ser Trp Ser Phe Asp Ala Leu Asn Glu Ile
    130                 135                 140
Met Leu Gly Ile Glu Glu Phe His Glu Pro Thr Glu Glu Gln Ile Ala
145                 150                 155                 160
Lys Gly Ala Gln Tyr Ala Asp Glu Tyr His Gly Arg Asp Gly Val Val
                165                 170                 175
Gln Val Ser Phe Pro Ala Gly Met Phe Gly Gly Ile Gln Leu Ser Ala
            180                 185                 190
Leu Glu Ala Ser Thr Leu Val Trp Lys Gly Leu Lys Leu Val Ala Asp
        195                 200                 205
Phe Ala Ala Gly Val Thr Ser Gly Ala Thr Ile Ile Pro Asn Met Val
    210                 215                 220
Glu Pro Asn Asp Ser Gln Asn Arg Ser Pro Phe Thr Val Tyr Ala
225                 230                 235                 240
Lys His Gln Thr Gln Glu Arg Ser Asn Phe Leu Ile Leu Thr Gly His
                245                 250                 255
Arg Val Thr Ser Ile Asn Trp Arg Asn Gly Thr Gly Met Val Ala Asp
            260                 265                 270
Gly Val Thr Phe Gln Ala Cys Arg Glu Cys Glu Val His Thr Ala Thr
        275                 280                 285
Thr Lys Arg Glu Val Leu Leu Ala Ala Gly Ser Leu Gln Ser Pro Gln
    290                 295                 300
Leu Leu Glu Leu Ser Gly Val Gly Asp Pro Glu Val Leu Ala Ala Ala
305                 310                 315                 320
Tyr Val Pro Leu Lys Leu Cys Ser Pro Asn Val Gly Lys Asn Met Gln
                325                 330                 335
Glu Gln Thr Lys Asn Thr Leu Trp Phe Asp Pro Ile Ser Thr Asp Phe
            340                 345                 350
Asp Gly Ser Gly Pro Pro Asn Ala Val Ala Phe Pro Asp Val His Gln
        355                 360                 365
Leu Phe Lys Asn Asp Ser Ala Ser Ile Tyr Lys Ser Ile Ile Ser Ser
    370                 375                 380
Leu Glu Gly Tyr Ser Gln Asn Leu Thr Ala Ala Gly Ile Val Thr Asn
385                 390                 395                 400
Ala Thr Ala Thr Arg Leu Ile Leu Glu Ala Gln Val Asn Asn Leu Trp
                405                 410                 415
Lys Asp Asn Ala Gly Ala Ala Glu Ile Phe Phe Val Thr Ser Pro Thr
            420                 425                 430
Thr Gly Gln Val Gly Ile Asp Leu Trp Asn Leu Ile Val Leu Ser Arg
        435                 440                 445
Gly Tyr Val His Ile Thr Ser Asn Ser Ser Trp Asp His Pro Gln Ile
    450                 455                 460
Glu Pro Ser Tyr Phe Gly His Pro Phe Asp Leu Glu Ile Gln Leu Ala
465                 470                 475                 480
Ala Thr Lys Gln Ser Arg Glu Val Ser Gln Thr Glu Pro Leu Ala Ser
                485                 490                 495
Leu Ile Ser Ala Glu Thr Phe Pro Gly Phe Asp Glu Val Pro Gln Asn
            500                 505                 510
Ala Thr Asp Asp Val Trp Glu Gln Trp Val Lys Glu Thr Phe Thr Ser
        515                 520                 525
Val Trp His Tyr Ile Ala Thr Leu Gly Met Met Lys Glu Glu Leu Gly
    530                 535                 540
```

```
Gly Val Val Asp Ser Arg Leu Lys Val Tyr Gly Ile Glu Asn Val Arg
545                 550                 555                 560

Ala Val Asp Ala Ser Val Leu Pro Ile Gln Leu Ser Ala His Leu Ser
                565                 570                 575

Ser Ser Leu Tyr Gly Ile Ala Glu Lys Ala Ala Met Met Ile Lys Glu
                580                 585                 590

Asp Gln Gly His
            595

<210> SEQ ID NO 3
<211> LENGTH: 1842
<212> TYPE: DNA
<213> ORGANISM: Cladosporiumneopsychrotolerns SL-16

<400> SEQUENCE: 3
atgcattcga ttcatttcct agctgctttc ctggctgcag tctctgaagc tcttcccaat      60
caaacgcgag ctgacaaagc ccatgccatc actacaaacg tcgaccaggt ctcaaacaaa     120
actttcgact acatagtctg cggcggaggc ttgacaggcc tggtcgtcgc aagtcggttg     180
tcagaagacc caaatatatc tgttctcgtc attgagaacg agaggacga ccacgaagac      240 cctcgcgtga acgacgtgag aacctacgga gaagccttca atccgacct cgactacaac      300 ctcacatcaa ccccagtacc atggcagaac gacacaggtc tacttcttgt ggctggcagg     360
acacttggtg aagtggcag tctcaatggt gccagctgga ctaaaggcga caggacgcag      420
tatgatttgc tcccggtctt gagcggcgat gactcgtggt ccttcgatgc tttgaacgag     480
atcatgctag gcattgaaga gttccacgaa ccgactgaag aacagattgc caaaggtgca     540
cagtatgcag acgaatacca tggccgtgac ggagttgtcc aagtctcctt cccagctggc     600
atgttcggcg gcattcaact ttcggctttg aagcttcca ctctcgtctg aagggcctg       660 aaacttgtcg cggactttgc agccggagtg acaagtggtg cgaccatcat cccaaacatg     720
gttgagccaa cgactccca aaatcggtct tccccattca cggtctatgc caagcaccag      780
actcaggaac gcagcaactt cttgatcttg acaggacacc gtgtgacatc catcaactgg     840
cgcaacggca ctggcatggt agctgatggt gtcacatttc aagcatgccg cgaatgcgag     900
gtacacacag ccacgacaaa gcgagaagta ctgctcgccg cgggctcgtt gcagagccca     960
cagcttctcg agctctctgg cgtgggtgat cctgaggtct tggccgccgc atatgttcct    1020
ctgaagctgt gttctcccaa tgttggtaag aacatgcagg aacagaccaa aaacactctc    1080
tggttcgacc ccatcagcac cgatttcgat ggttccggac ctccaaacgc agttgctttc    1140
ccggacgtcc accaactgtt caaaaatgac agtgcaagca tttacaaatc tatcatttcc    1200
agcctcgaag gatactcaca aaacctgacc gccgccggca tcgtcacaaa cgccacagca    1260
acacgcctca tccttgaagc acaagtcaac aacctctgga agataacgc cggagcagca    1320 gagatcttct tcgtgacttc acccaccaca ggccaagttg gcattgatct ctggaacctc    1380
atcgtcctgt cccgaggcta cgtgcacatc acttcgaact cctcctggga ccaccccaa    1440 atcgagccct cctacttcgg ccacccttc gaccttgaga ttcagctcgc agccaccaag    1500
caatcacgcg aagtctccca aacagaacct ctcgcctcgc tcatcagcgc cgagacattt    1560
cctggtttcg atgaagtgcc gcaaaatgcc acagacgatg tgtgggagca gtgggttaag    1620
gagacgttca catctgtttg gcactacata gctacattgg gcatgatgaa agaggaattg    1680
ggtggtgttg tggacagcag gctgaaggta tatggcattg agaatgtacg agcggtggat    1740
gctagtgtgc tgccgatcca gctttcggcg cacttgagct cttcgctgta cggcattgcg    1800
```
gagaaggctg ctatgatgat taaggaagat cagggacatt ga            1842

<210> SEQ ID NO 4
<211> LENGTH: 1791
<212> TYPE: DNA
<213> ORGANISM: Cladosporiumneopsychrotolerns SL-16

<400> SEQUENCE: 4
cttcccaatc aaacgcgagc tgacaaagcc catgccatca ctacaaacgt cgaccaggtc    60
tcaaacaaaa ctttcgacta catagtctgc ggcggaggct tgacaggcct ggtcgtcgca   120
agtcggttgt cagaagaccc aaatatatct gttctcgtca ttgagaacgg agaggacgac   180
cacgaagacc ctcgcgtgaa cgacgtgaga acctacggag aagccttcaa atccgacctc   240
gactacaacc tcacatcaac cccagtacca tggcagaacg acacaggtct acttcttgtg   300
gctggcagga cacttggtgg aagtggcagt ctcaatggtg ccagctggac taaaggcgac   360
aggacgcagt atgatttgct cccggtcttg agcggcgatg actcgtggtc cttcgatgct   420
ttgaacgaga tcatgctagg cattgaagag ttccacgaac cgactgaaga acagattgcc   480
aaaggtgcac agtatgcaga cgaataccat ggccgtgacg gagttgtcca agtctccttc   540
ccagctggca tgttcggcgg cattcaactt tcggctttgg aagcttccac tctcgtctgg   600
aagggcctga acttgtcgc ggactttgca gccggagtga caagtggtgc gaccatcatc   660
ccaaacatgg ttgagccaaa cgactcccaa aatcggtctt ccccattcac ggtctatgcc   720
aagcaccaga ctcaggaacg cagcaacttc ttgatcttga caggacaccg tgtgacatcc   780
atcaactggc gcaacggcac tggcatggta gctgatggtg tcacatttca agcatgccgc   840
gaatgcgagg tacacacagc cacgacaaag cgagaagtac tgctcgccgc gggctcgttg   900
cagagcccac agcttctcga gctctctggc gtgggtgatc ctgaggtctt ggccgccgca   960
tatgttcctc tgaagctgtg ttctcccaat gttggtaaga acatgcagga acagaccaaa   1020
aacactctct ggttcgaccc catcagcacc gatttcgatg gttccggacc tccaaacgca   1080
gttgctttcc cggacgtcca ccaactgttc aaaaatgaca gtgcaagcat ttacaaatct   1140
atcatttcca gcctcgaagg atactcacaa aacctgaccg ccgccggcat cgtcacaaac   1200
gccacagcaa cacgcctcat ccttgaagca caagtcaaca acctctggaa agataacgcc   1260
ggagcagcag agatcttctt cgtgacttca cccaccacag gccaagttgg cattgatctc   1320
tggaacctca tcgtcctgtc ccgaggctac gtgcacatca cttcgaactc ctcctgggac   1380 caccccaaa tcgagccctc ctacttcggc caccctttcg accttgagat tcagctcgca   1440
gccaccaagc aatcacgcga agtctcccaa acagaacctc tcgcctcgct catcagcgcc   1500
gagacatttc ctggtttcga tgaagtgccg caaaatgcca cagacgatgt gtgggagcag   1560
tgggttaagg agacgttcac atctgtttgg cactacatag ctacattggg catgatgaaa   1620
gaggaattgg gtggtgttgt ggacagcagg ctgaaggtat atggcattga gaatgtacga   1680
gcggtggatg ctagtgtgct gccgatccag cttccggcgc acttgagctc ttcgctgtac   1740
ggcattgcgg agaaggctgc tatgatgatt aaggaagatc agggacattg a            1791

<210> SEQ ID NO 5
<211> LENGTH: 40
<212> TYPE: DNA
<213> ORGANISM: Artificial Sequence
<220> FEATURE:
<223> OTHER INFORMATION: primer

```
<400> SEQUENCE: 5
actgaattcc ttcccaatca aacgcgagct gacaaagccc                                    40

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
gagtgcggcc gctcaatgtc cctgatcttc cttaatcatc                                    40
```